(12) United States Patent
Tarutani et al.

(10) Patent No.: US 9,856,269 B2
(45) Date of Patent: Jan. 2, 2018

(54) METHOD FOR PRODUCING PYROMELLITIC DIANHYDRIDE, PYROMELLITIC DIANHYDRIDE PRODUCED BY THE METHOD, AND APPARATUS THEREFOR

(71) Applicant: L'Air Liquide, Société Anonyme pour l'Etude et l'Exploitation des Procédés Georges Claude, Paris (FR)

(72) Inventors: Kohei Tarutani, Tokyo (JP); Takashi Kameoka, Tokyo (JP); Tomoko Yanagita, Tokyo (JP); Ryohei Matsui, Tokyo (JP)

(73) Assignee: L'Air Liquide, SociétéAnonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 14/916,498

(22) PCT Filed: Sep. 1, 2014

(86) PCT No.: PCT/JP2014/004482
§ 371 (c)(1),
(2) Date: Mar. 3, 2016

(87) PCT Pub. No.: WO2015/029457
PCT Pub. Date: Mar. 5, 2015

(65) Prior Publication Data
US 2016/0214991 A1     Jul. 28, 2016

(30) Foreign Application Priority Data

Sep. 2, 2013 (JP) ................................. 2013-181124

(51) Int. Cl.
*C07D 493/04* (2006.01)
(52) U.S. Cl.
CPC .................. *C07D 493/04* (2013.01)
(58) Field of Classification Search
None
See application file for complete search history.

(56) References Cited

U.S. PATENT DOCUMENTS

| | | | |
|---|---|---|---|
| 4,376,195 A | 3/1983 | Lee | |
| 6,476,238 B1 | 11/2002 | Chu et al. | |
| 7,569,707 B2 * | 8/2009 | Ogawa | C07C 51/56 |
| | | | 549/239 |
| 2004/0016404 A1 | 1/2004 | Gregg et al. | |
| 2007/0021622 A1 | 1/2007 | Ogawa et al. | |
| 2010/0255198 A1 | 10/2010 | Cleary et al. | |
| 2012/0180719 A1 | 7/2012 | Inoue et al. | |
| 2013/0178597 A1 | 7/2013 | Takasawa et al. | |

FOREIGN PATENT DOCUMENTS

| | | |
|---|---|---|
| EP | 1 746 081 | 1/2007 |
| EP | 2 361 672 | 8/2011 |
| GB | 1 280 562 | 7/1972 |
| JP | S59 199683 | 11/1984 |
| JP | H05 1069 | 1/1993 |
| JP | 2006 503178 | 1/2006 |

OTHER PUBLICATIONS

International Search Report and Written Opinion for corresponding PCT/JP2014/004482, dated Oct. 31, 2014.

\* cited by examiner

*Primary Examiner* — Heidi Reese
(74) *Attorney, Agent, or Firm* — Patricia E. McQueeney

(57) ABSTRACT

A method for producing a highly pure PMDA comprises at least the following steps: (1) a step of preparing a raw material solution by dissolving a raw material of a pyromellitic dianhydride in an acetic acid solvent, (2) a step of preparing a precursor pyromellitic dianhydride by recrystallizing the pyromellitic dianhydride in the prepared raw material solution and separating the acetic acid solvent, (3) a step of performing a degassing treatment on the precursor pyromellitic dianhydride by stirring the precursor pyromellitic dianhydride in a fluidized state while heating under reduced-pressure conditions, and (4) a step of taking out the pyromellitic dianhydride subjected to the degassing treatment.

12 Claims, 11 Drawing Sheets

[Fig. 1A]
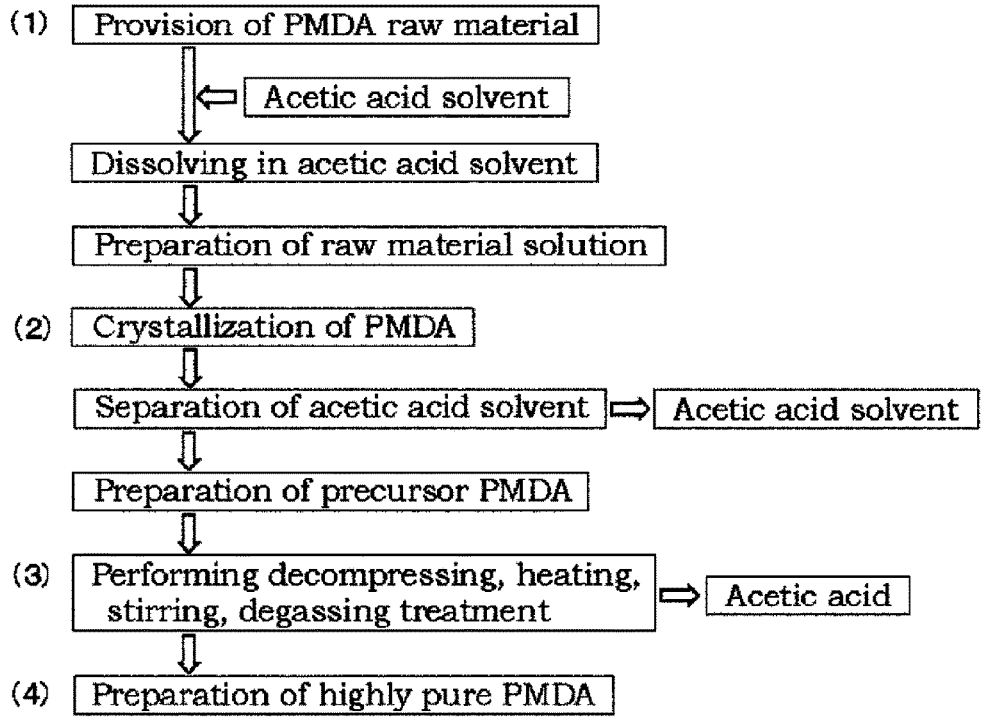
[Fig. 1B]
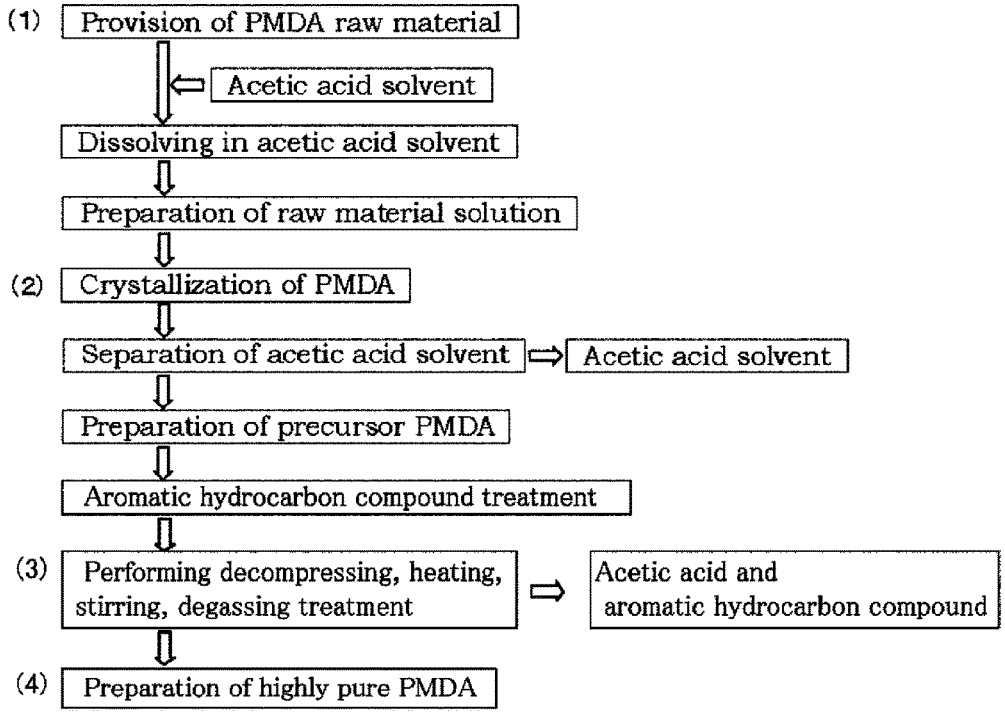

[Fig. 2]
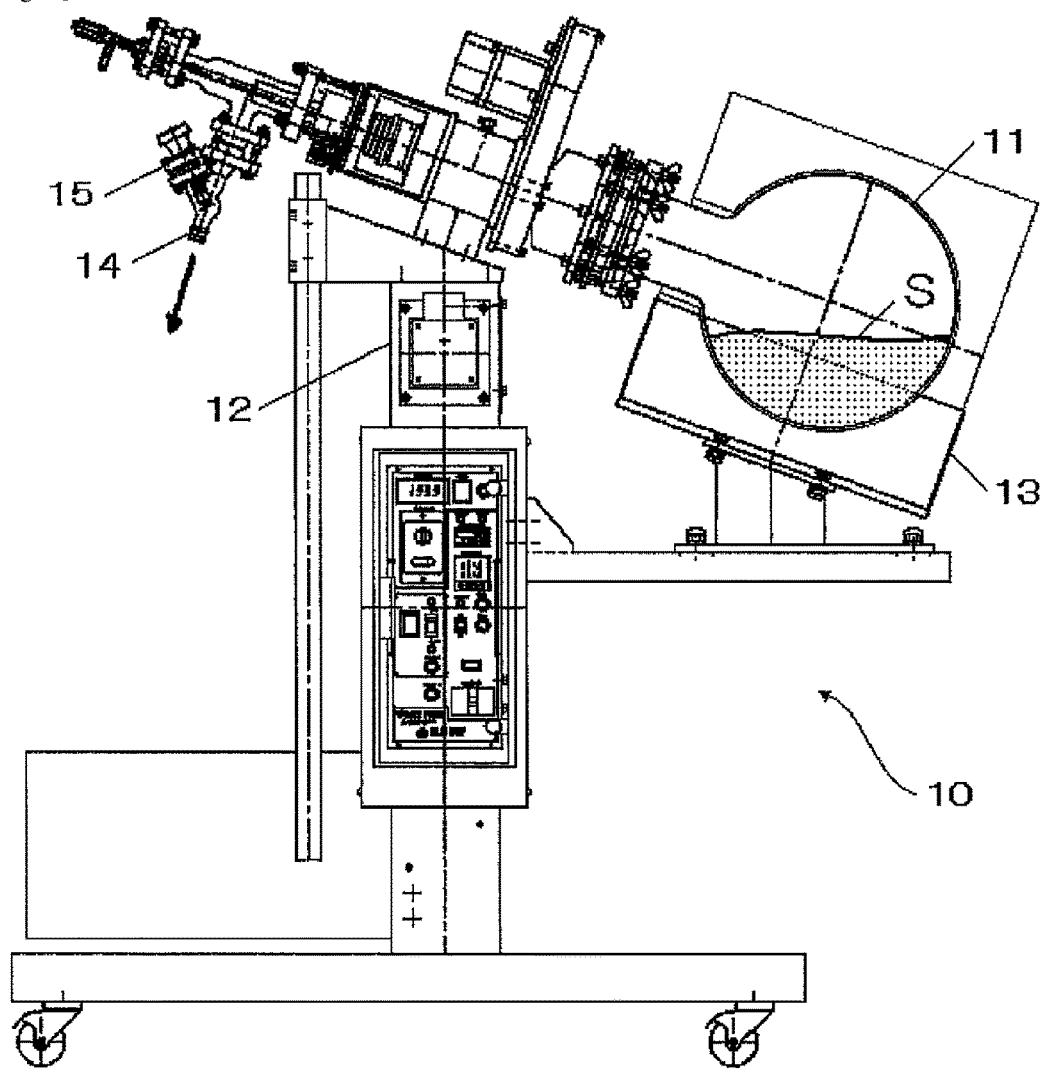

[Fig. 3A]
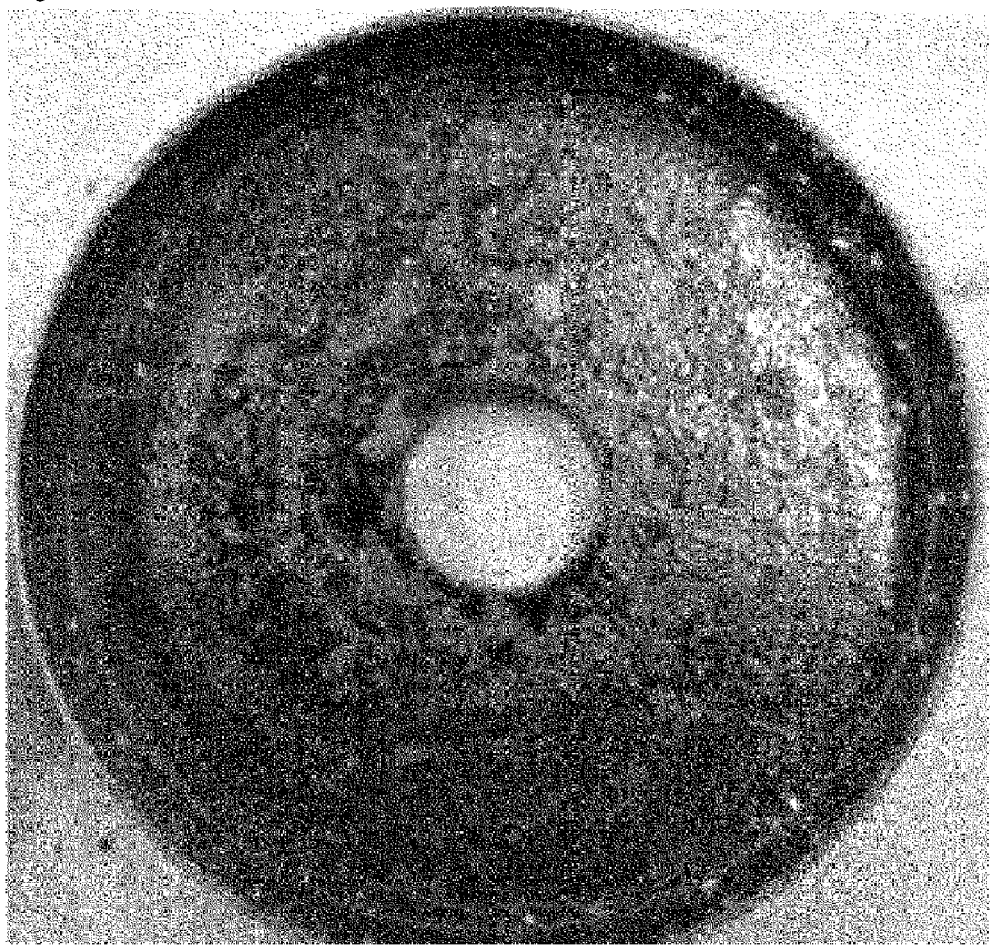

[Fig. 3B]
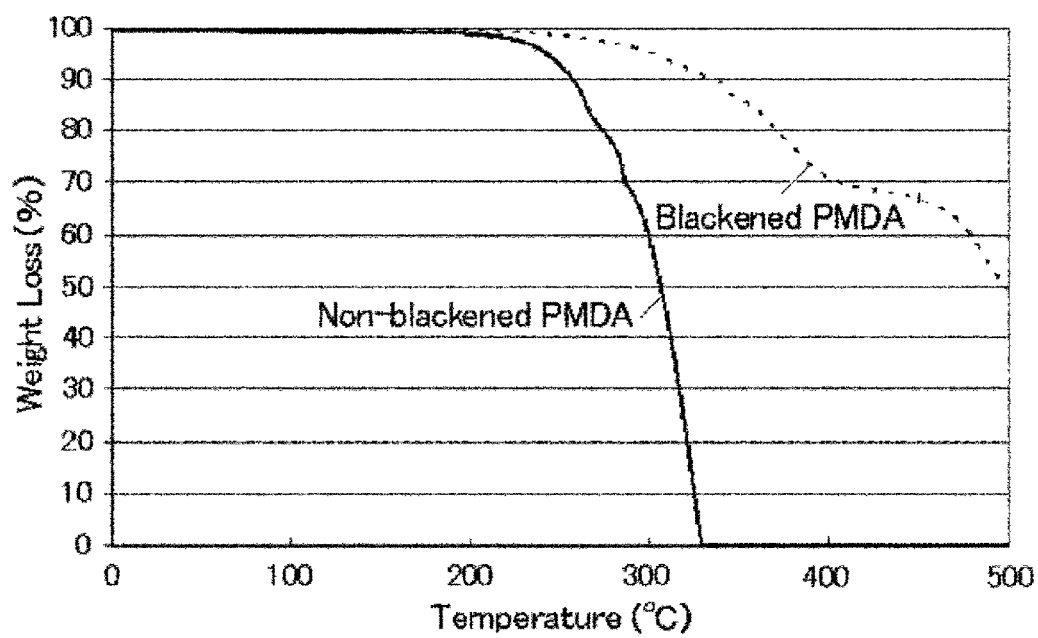

[Fig. 4A]
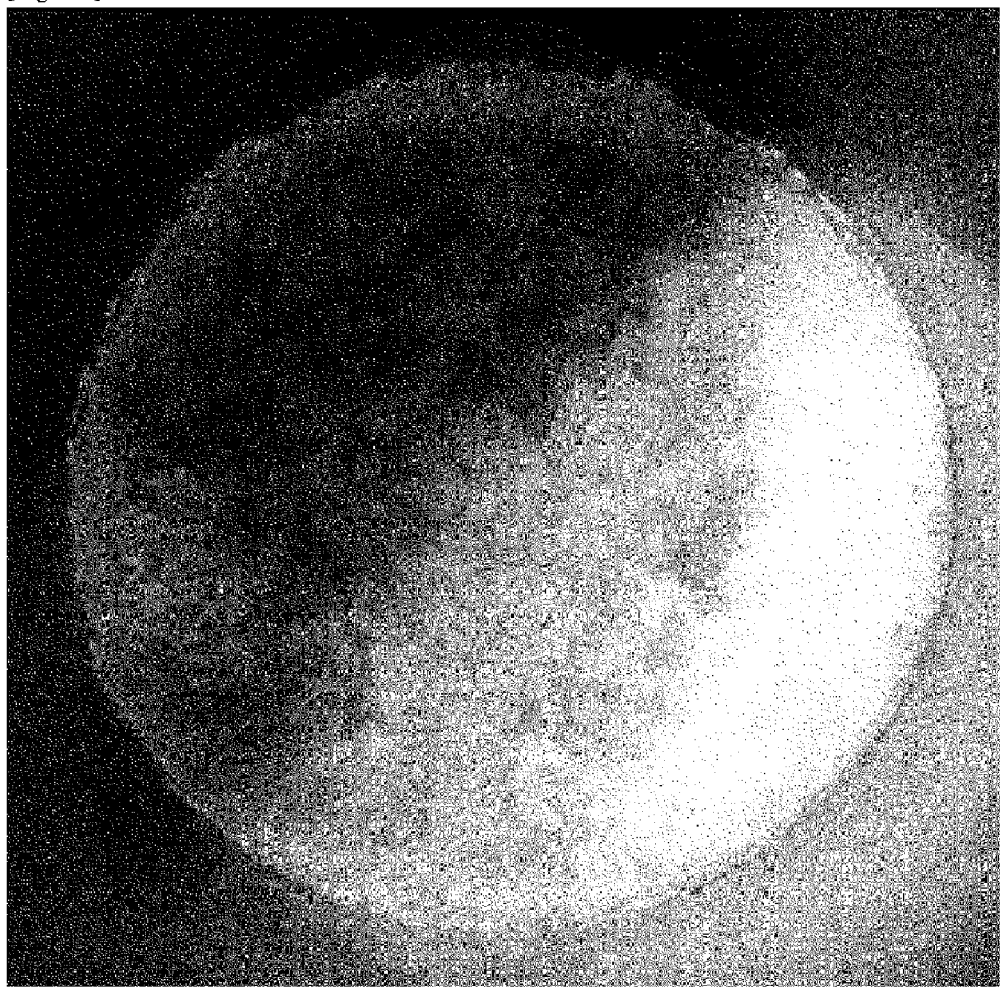

[Fig. 4B]
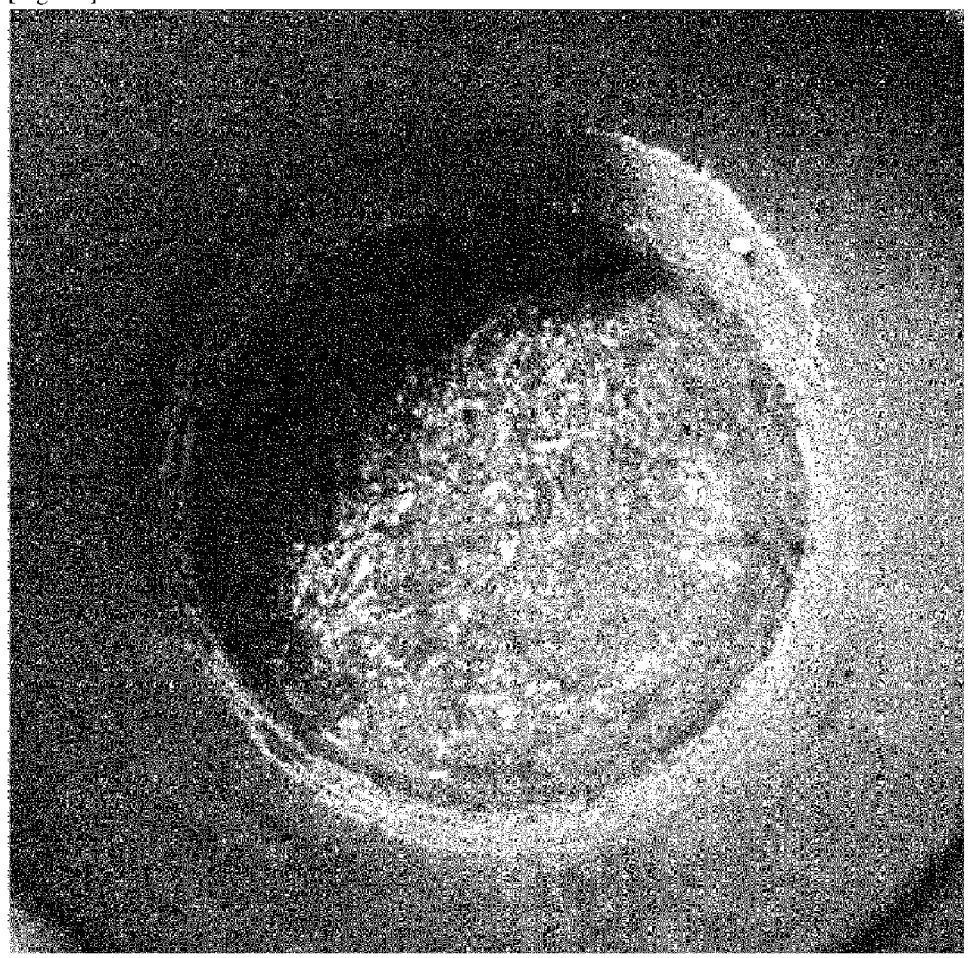

[Fig. 5]
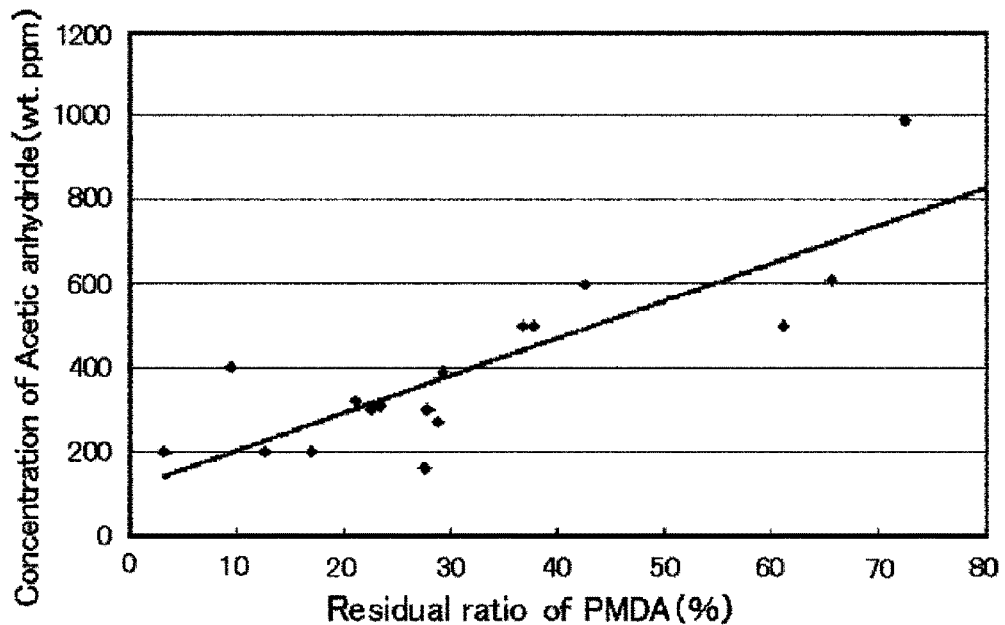
[Fig. 6]
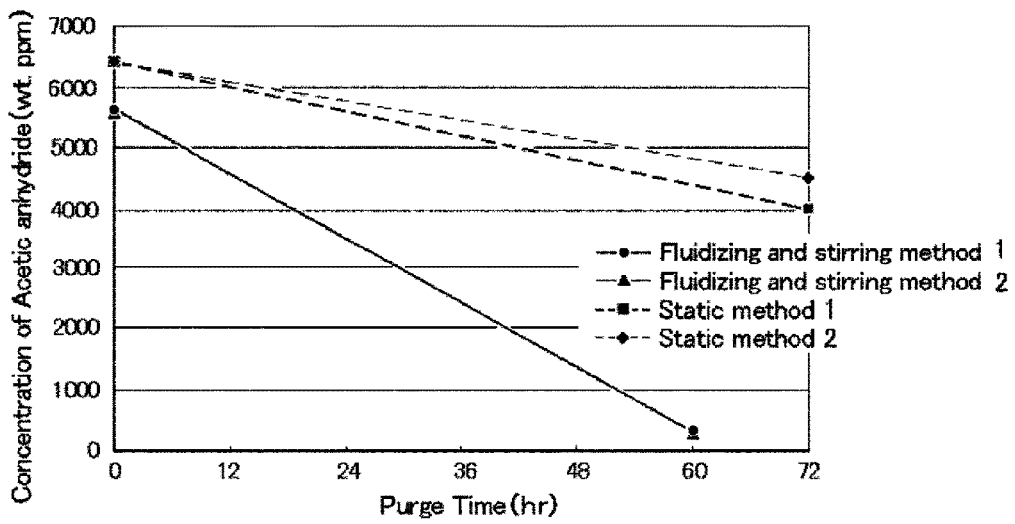

[Fig. 7]
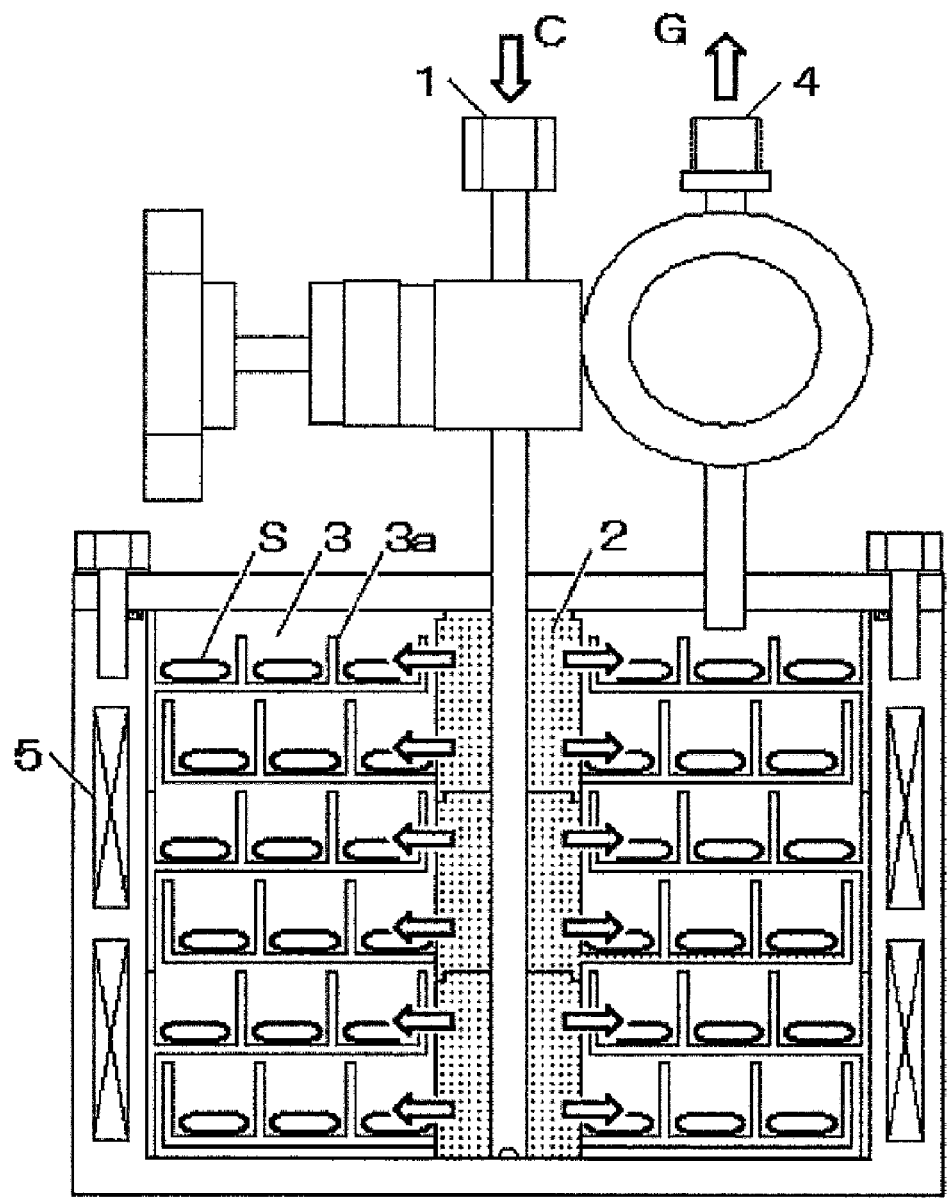

[Fig. 8]
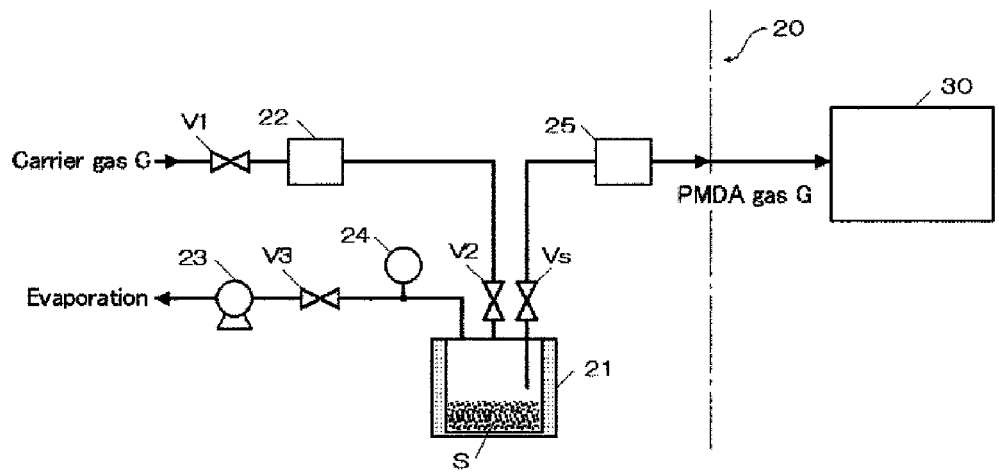
[Fig. 9]
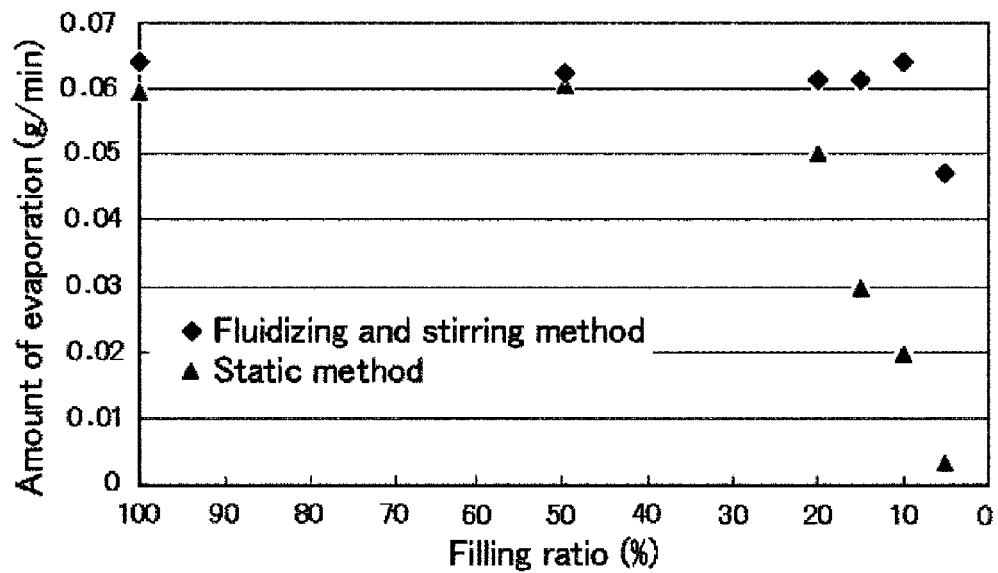

[Fig. 10A]
(A)
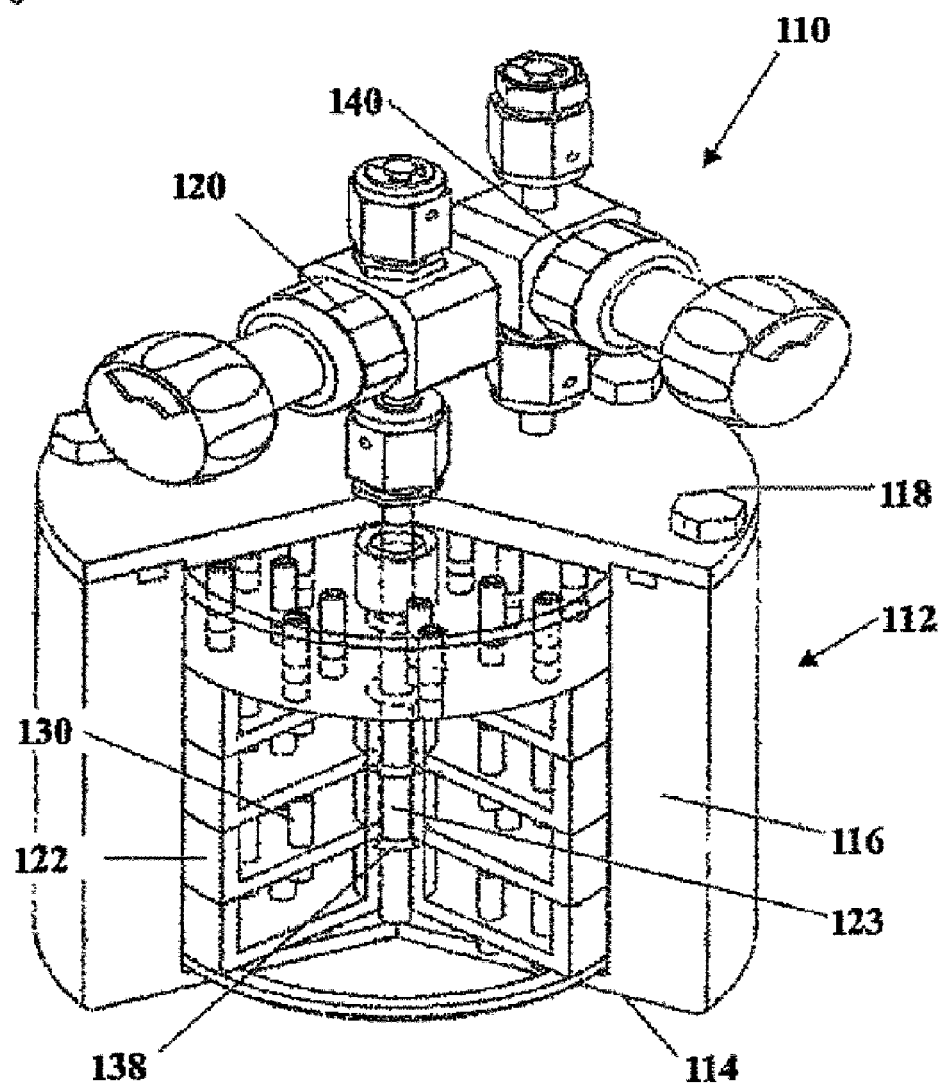

[Fig. 10B]
(B)
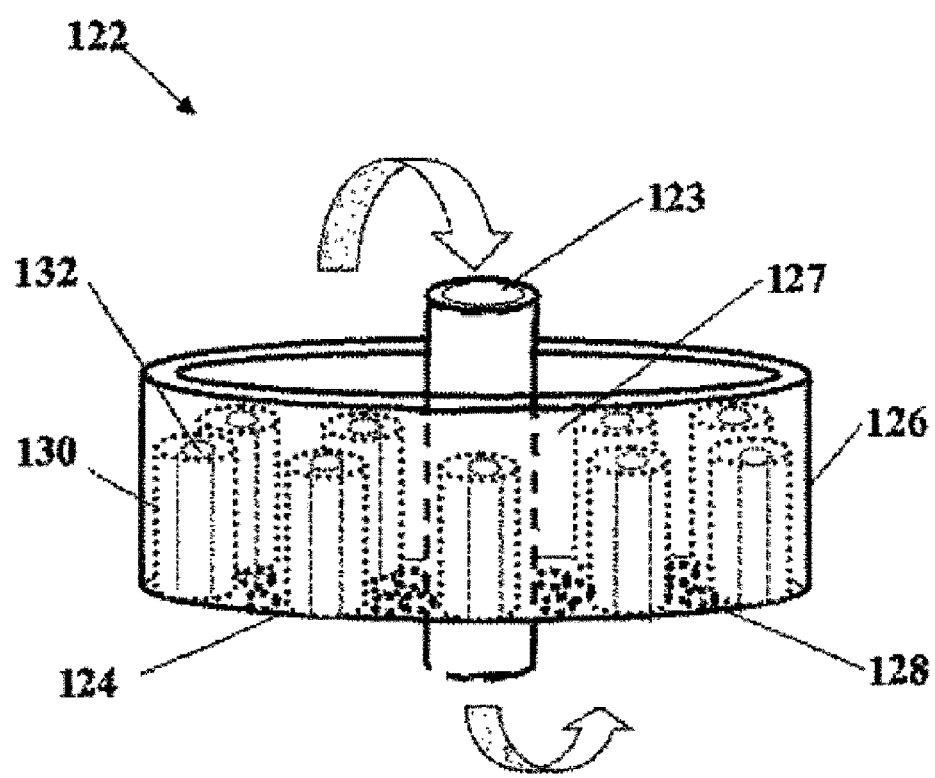

METHOD FOR PRODUCING PYROMELLITIC DIANHYDRIDE, PYROMELLITIC DIANHYDRIDE PRODUCED BY THE METHOD, AND APPARATUS THEREFOR

This application is a 371 of International PCT Application PCT/JP2014/004482, filed Sep. 1, 2014, which claims priority to Japanese patent application 2013-181124 filed Sep. 2, 2013, the entire contents of each being incorporated herein by reference.

TECHNICAL FIELD

The present invention relates to a method for producing pyromellitic dianhydride, a pyromellitic dianhydride produced by the method, a method for supplying a pyromellitic dianhydride, and an apparatus for supplying a pyromellitic dianhydride.

BACKGROUND ART

Pyromellitic dianhydride (which may hereafter be referred to as "PMDA") is often used in a production apparatus for producing semiconductors, solar cells, and the like, or in research equipment for developing new materials, as a material for forming semiconductor films that are demanded to be highly pure products. PMDA is often used in a gas phase by being heated and sublimated at a predetermined temperature, and is sublimated and transported by an inert gas having a low reactivity and a high stability such as a rare gas such as helium or argon, so as to be supplied to the above production apparatus and consumed.

In particular, when PMDA is used as a raw material for a polyimide resin having a high heat resistance, a crosslinking agent for foamed polyester, a special plasticizer, or the like, highly pure pyromellitic dianhydride is demanded, and various production methods are proposed. For example, there is a method for producing a pyromellitic dianhydride comprising a step of thermally dehydrating crude pyromellitic acid in the absence of acetic anhydride to convert 50.0 to 99.5 wt % of the pyromellitic acid into pyromellitic dianhydride and affording a reaction mixture containing at least pyromellitic acid and pyromellitic dianhydride and a step of thermally dehydrating the reaction mixture in the presence of acetic anhydride (See, for example, JP-A-2013-006856).

In addition, as a method for supplying such highly pure pyromellitic dianhydride, various supplying methods and supplying apparatus are proposed due to the special handling properties of the pyromellitic dianhydride. For example, there is a construction example of an evaporator delivery system 110, as shown in FIGS. 10A and 10B, having numerous containers that provide an enlarged surface area for evaporation of liquid and solid materials such as liquid and solid source reagents used in the chemical vapor deposition (CVD) method, the atomic layer chemical vapor deposition (ALCVD) method, and the ion injection method (See, for example, JP-A-2006-503178). In an ampule 112, a plurality of vertically stacked containers 122 including a bottom 114 and a side wall 116 that form an inner chamber are placed in an inner chamber of the ampule. The stacked containers are separable from each other and removable from the ampoule for easy cleaning and refilling. An internal carrier gas member 123 is placed in the ampule, and this internal carrier gas member 123 is connected (welded) to a carrier gas inlet 120 to guide a carrier gas to the bottom of the inner chamber and under the lowermost container of the vertically stacked containers. The internal carrier gas member 123 passes through each of a container cavity 127 and a container bottom 124. The individual containers 122 are each provided with the bottom 124 and a side wall 126, so as to form a container cavity 127 for placing preferable source materials 128. Each of the individual containers includes a plurality of protrusions 130, and each protrusion includes a passageway 132 along which the carrier gas moves by passing through the protrusion (See paragraphs 0018 to 0023 of JP-A-2006-503178). Here, reference numeral 138 denotes an O-ring for sealing and reference numeral 140 denotes a gas outlet valve.

SUMMARY OF INVENTION

Technical Problem

However, in the method for producing a pyromellitic dianhydride (PMDA) as described above, the following problems may be raised.

(i) In the crude PMDA, a slight amount of metal components and moisture are inevitably mingled in the process of production thereof, and such metal components and moisture may sometimes give adverse effects on the insulation property and the like in a formed film using PMDA, thereby necessitating a further purification treatment.

(ii) In such PMDA after the purification, acetic anhydride, glacial acetic acid, and the like used as a solvent in the process of production thereof remain. This often invites denaturing (blackening) of the material and the like at the time of sublimation and supply at a high temperature, leading to decrease in the amount of evaporation and decrease in the usage ratio of the material.

In addition, in the apparatus (method) for supplying PMDA, the following problems may be raised.

(iii) In transporting and supplying such PMDA containing acetic anhydride and the like or moisture after evaporation, there is a fear that denatured PMDA may adhere in a flow passageway for transportation, thereby generating a situation in which the amount of supply cannot be sufficiently controlled, or partial clogging of the flow passageway.

(iv) Generally, with respect to a solid material such as PMDA, the component concentration (material concentration) of PMDA or the like in a supplied gas is liable to be affected by the area of contact with a carrier gas, so that the material concentration tends to be unstable due to a short-cut path of the carrier gas or local unevenness of the flow rate. In accordance with the decrease in the residual amount of PMDA in the container, the material concentration in the carrier gas decreases.

(v) In the construction of the evaporator delivery system 110, the material configuration on a tray may become nonuniform when the container is tilted, thereby raising a fear that the material concentration may become unstable. Besides this, there are problems in that, because the container structure is complex, filling with the material and washing of the container are not convenient.

(vi) Generally, as a method for sensing a residual amount of a filling material, pressure measurement is widely used in the case of a gas material, and a liquid-level gauge is widely used in the case of a liquid material. Because the uniformity of the material is high, these sensors can sense with a high precision. On the other hand, in the case of a solid material such as PMDA, weight measurement or a method of accumulating the concentration of the supplying material and the supplying time is used. However, in order to ensure a stable material concentration, it may be demanded that the material is stored in a space having a predetermined volume and stable time by diffusion is ensured. In the weight measurement, change in the material concentration accompanying the local decrease of PMDA cannot be sensed and, because the container is connected to a pipe and the container is generally placed in a heated environment, the measurement errors are large. Further, for measurement of the material concentration, a sensing device of supersonic type, thermal conductivity type, infrared type, or the like is needed.

An object of the present invention is to provide a method for producing a highly pure PMDA that can be evaporated at a stable concentration for a long period of time by a convenient procedure and construction, as well as PMDA produced by the method. Another object of the present invention is to provide a method and an apparatus for supplying PMDA that can supply PMDA at a stable concentration for a long period of time.

Solution to Problem

As a result of repetitive eager researches in order to solve the aforementioned problems, the present inventors have found out that the aforementioned objects can be achieved by the method for producing PMDA, PMDA produced by the method, the method for supplying PMDA, and the apparatus for supplying PMDA described below, thereby completing the present invention.

The present invention of claim 1 relates to a method for producing a pyromellitic dianhydride comprising at least the following steps:

(1) a step of preparing a raw material solution by dissolving a raw material of a pyromellitic dianhydride in an acetic acid solvent, (2) a step of preparing a precursor pyromellitic dianhydride by recrystallizing the pyromellitic dianhydride in the prepared raw material solution and separating the acetic acid solvent, (3) a step of performing a degassing treatment on the precursor pyromellitic dianhydride by stirring the precursor pyromellitic dianhydride in a fluidized state while heating under reduced-pressure conditions, and (4) a step of taking out the pyromellitic dianhydride subjected to the degassing treatment.

PMDA has intrinsic properties as described in the aforementioned "problems". Therefore, in order to prepare a highly pure PMDA, it is demanded that suitable and sufficient handling conditions are set in the production steps. In a verification process thereof, the present inventors have obtained a variety of findings on the "blackening of PMDA under high-temperature conditions and decrease in the amount of evaporation" and have found out an effective method for removing acetic anhydride and glacial acetic acid (which may hereafter referred to as "acetic anhydride and the like") remaining in PMDA that are caused by an acetic acid solvent essential for removing impurities such as metal components and moisture mingled in the preparation of a crude PMDA. Specifically, precursor PMDA having no impurities and having a small amount of acetic anhydride and the like can be prepared by recrystallization of PMDA dissolved in the acetic acid solvent, and PMDA having an extremely high purity can be prepared by stirring in a fluidized state while heating under reduced-pressure conditions and by performing a degassing treatment. This makes it possible to provide a method for producing a highly pure PMDA that can be evaporated at a stable concentration for a long period of time.

The present invention of claim 2 relates to the method for producing a pyromellitic dianhydride according to claim 1, further comprising a step of bringing the recrystallized precursor pyromellitic dianhydride into contact with a substituted or unsubstituted aromatic hydrocarbon compound. It is important to remove acetic acid as much as possible in order to produce highly pure PMDA. The present inventors have conducted studies regarding more effective acetic acid removal conditions and technical effects thereof. Specifically, the present inventors have found conditions under which acetic acid in the recrystallized precursor PMDA can be effectively removed by bringing the recrystallized precursor PMDA into contact with a substituted or unsubstituted aromatic hydrocarbon compound to produce PMDA with higher purity.

The present invention of claim 3 relates to the method for producing a pyromellitic dianhydride according to claim 2, wherein, the step of bringing the recrystallized precursor pyromellitic dianhydride into contact with the substituted or unsubstituted aromatic hydrocarbon compound is performed between the step (2) and the step (3), and brings the precursor pyromellitic dianhydride into contact with the substituted or unsubstituted aromatic hydrocarbon compound. It is possible to more efficiently remove acetic acid in the precursor PMDA by bringing the substituted or unsubstituted aromatic hydrocarbon compound into contact with the crystallized pyromellitic dianhydride after separating the acetic acid solvent.

The present invention of claim 4 relates to the method for producing a pyromellitic dianhydride according to any one of claims 1 to 3, wherein, in the step (1), the raw material solution is prepared under heated conditions of about 140 degrees C., which is a boiling point of the acetic acid solvent, or lower; in the step (2), the raw material solution is cooled to an ordinary temperature to recrystallize the pyromellitic acid; in the step (3), the degassing treatment is carried out under heated conditions of about 120 degrees C., which is a boiling point of acetic acid, or higher and about 290 degrees C., which is a melting point of pyromellitic dianhydride, or lower and under reduced-pressure conditions of 100 Torr or lower; and in the step (4), cooling and pressure-raising are carried out to prepare a powder and granular pyromellitic dianhydride that is present under ordinary-temperature and ordinary-pressure conditions. In the steps of preparing highly pure PMDA, the coexistence conditions of acetic acid and PMDA are an extremely important factor. In the present invention, operation conditions in each preparation step have been closely checked, and optimum processing conditions and the technical effects thereof have been verified. In other words, it has been made possible to prepare PMDA having a further higher purity by optimizing the temperature conditions and the like for recrystallization during the degassing treatment in the preparation of precursor PMDA and further by optimizing the reduced-pressure conditions, heating conditions, and fluidizing and stirring conditions.

The present invention of claim 5 relates to the method for producing a pyromellitic dianhydride according to any one of claims 1 to 4, wherein, in the step (2), a powder and granular precursor pyromellitic dianhydride is prepared by recrystallizing while stirring the raw material solution and separating the acetic acid solvent; and in the step (4), a powder and granular pyromellitic dianhydride is prepared in an inert gas atmosphere. By such a construction, the step of preparing the precursor PMDA and the degassing treatment step can be further optimized, and PMDA having a further higher purity can be prepared.

The present invention relates to the pyromellitic dianhydride produced by the method for producing a pyromellitic dianhydride according to any one of claims 1 to 5, wherein a concentration of acetic acid contained is 400 mass ppm or less. As described above, PMDA having a high purity not present in the past can be prepared by the method for producing PMDA according to the present invention. In such a verification process, the present inventors have obtained a finding related to correlation between the decrease in the evaporation amount of PMDA and the concentration of acetic acid contained, in the case of sublimating and evaporating PMDA prepared by using such a production method and supplying the obtained PMDA to consumption equipment or the like. In other words, by definitizing an objective standard that can reduce the decrease in the evaporation amount, the present invention has made it possible to supply PMDA having extremely excellent properties and to achieve an improvement in the practicality thereof.

The present invention relates to an apparatus for supplying a pyromellitic dianhydride, wherein the pyromellitic dianhydride produced by the production method according to any one of claims 1 to 5 or the pyromellitic dianhydride according to claim 6 is used; the apparatus comprises a sample placing unit for placing a sample tray into which the pyromellitic dianhydride is charged, a supplying unit for supplying a carrier gas, a dispersing unit for dispersing the supplied carrier gas, and an outputting unit for delivering a gaseous pyromellitic dianhydride prepared in the sample placing unit; and the powder and granular pyromellitic dianhydride placed in the sample placing unit is evaporated under predetermined temperature conditions, dispersed under atmospheric pressure or reduced-pressure conditions of a carrier gas atmosphere to be entrained by the carrier gas, and outputted as a gaseous pyromellitic dianhydride. The present invention relates to a method for supplying a pyromellitic dianhydride that uses the pyromellitic dianhydride produced by the production method according to any one of claims 1 to 5 or the pyromellitic dianhydride according to claim 6 and uses the apparatus for supplying a pyromellitic dianhydride according to claim 7, and comprises the following steps: (1) a step of providing a powder and granular pyromellitic dianhydride, (2) a step of placing in the sample placing unit a sample tray into which the powder and granular pyromellitic dianhydride is charged, (3) a step of supplying a carrier gas to the supplying unit, (4) a step of heating the sample placing unit in the carrier gas atmosphere to temperature conditions corresponding to a desired vapor pressure of pyromellitic dianhydride, and (5) a step of outputting a gaseous pyromellitic dianhydride entrained by the supplied carrier gas under desired predetermined pressure conditions.

As described above, there have been some problems in evaporating or sublimating PMDA to supply PMDA gas having a stable concentration. The present invention has made it possible to ensure PMDA that can be evaporated with certainty at a stable concentration for a long period of time first by providing a method for producing a highly pure PMDA that can be stably evaporated and definitizing a property standard of PMDA prepared the method. Further, the present invention makes it possible to take out PMDA gas having a uniform concentration by dispersing a carrier gas that is brought into contact with such PMDA to form a uniform flow, evaporating or sublimating PMDA uniformly, and bringing PMDA into contact with the dispersed carrier gas without generating an uneven distribution. In this manner, the present invention has made it possible to provide a method and an apparatus for supplying PMDA that can supply PMDA gas at a stable concentration for a long period of time by a convenient procedure and construction.

BRIEF DESCRIPTION OF DRAWINGS

FIG. 1A is a descriptive view exemplifying a procedure of preparing a highly pure PMDA according to the present invention;

FIG. 1B is a view showing a modification of a procedure of preparing a highly pure PMDA according to the present invention;

FIG. 2 is a schematic view illustrating a construction example of an apparatus for performing a degassing treatment in a step of preparing PMDA according to the present invention;

FIG. 3A is an outlook view showing PMDA blackened by being used under high-temperature conditions;

FIG. 3B is a descriptive view showing a result of performing a thermal analysis on blackened PMDA and non-denatured PMDA;

FIG. 4A is an outlook view showing blackened PMDA with respect to the difference in concentration of the acetic anhydride and the like contained (cf., FIG. 4B);

FIG. 4B is an outlook view showing non-denatured PMDA with respect to the difference in concentration of the acetic anhydride and the like contained (cf., FIG. 4A);

FIG. 5 is a descriptive view showing a relationship between the residual concentration of acetic anhydride and the like in PMDA and the residual ratio of PMDA after use;

FIG. 6 is a descriptive view showing a concentration change of acetic anhydride and the like in PMDA subjected to a degassing treatment according to the present invention;

FIG. 7 is a schematic view illustrating a construction example of an apparatus for supplying PMDA according to the present invention;

FIG. 8 is a schematic view illustrating an apparatus for supplying PMDA used for verification of the present invention;

FIG. 9 is a descriptive view showing a correlation between a filling ratio (ratio of residual amount) and amount of evaporation of PMDA; and FIG. 10A is a schematic view exemplifying an evaporator delivery system for evaporation of liquid and solid materials according to a conventional art.

FIG. 10B is a schematic view exemplifying an evaporator delivery system for evaporation of liquid and solid materials according to a conventional art.

DESCRIPTION OF EMBODIMENTS

Method for Producing Pyromellitic Dianhydride According to the Present Invention A method for producing a pyromellitic dianhydride (PMDA) according to the present invention (hereafter referred to as "present production method") comprises at least the following steps: (1) a step of preparing a raw material solution by dissolving a raw material of pyromellitic dianhydride in an acetic acid solvent, (2) a step of preparing a precursor pyromellitic dianhydride by recrystallizing the pyromellitic dianhydride in the prepared raw material solution and separating the acetic acid solvent, (3) a step of performing a degassing treatment on the precursor pyromellitic dianhydride by stirring the precursor pyromellitic dianhydride in a fluidized state while heating under reduced-pressure conditions, and (4) a step of taking out the pyromellitic dianhydride subjected to the degassing treatment. Hereafter, specific embodiments thereof will be described.

PMDA has a melting point of about 283 to 287 degrees C. and a boiling point of about 397 degrees C. and is one kind of a solid material that is sublimated (evaporated) at a predetermined temperature (for example, PMDA has a vapor pressure of about 0.66 kPa under conditions with a set temperature of 259 degrees C.). As described before, PMDA is widely used industrially as a material for forming films or the like. As described in the aforementioned "problems", PMDA has intrinsic properties. Therefore, in order to prepare highly pure PMDA, it is demanded that suitable and sufficient handling conditions are set in the production steps.

(Process for Preparing Highly Pure PMDA)

In a process for producing PMDA, powdery or granular crude PMDA (PMDA raw material) is recrystallized while removing impurities such as metal components and moisture with an acetic acid solvent, and the obtained recrystallized product is heated under reduced pressure and is stirred and degassed in a fluidized state to remove the residual acetic anhydride and the like, whereby a highly pure PMDA can be prepared. In accordance with a procedure exemplified in FIG. 1A, a highly pure PMDA is prepared by performing the following steps. The details thereof will be described.

(1) Step of Preparing a Raw Material Solution

First, PMDA raw material is provided and dissolved in an acetic acid solvent to prepare a raw material solution.

(1-1) Provision of PMDA Raw Material

A predetermined amount of PMDA raw material which is powdery or granular in an ordinary state is provided. In order to prevent mingling of impurities such as moisture, the following operations are preferably carried out in an inert gas atmosphere.

(1-2) Preparation of a Raw Material Solution

The PMDA raw material is dissolved in an acetic acid solvent to prepare a raw material solution. Here, as the acetic acid solvent, it is preferable to use a mixed solution of acetic anhydride and glacial acetic acid that can capture, by dissolving or the like, metal components and moisture that are present in a slight amount in PMDA raw material. During this operation, the solubility of PMDA raw material in the acetic acid solvent can be increased by preparing the raw material solution under heated conditions of about 140 degrees C., which is a boiling point of the acetic acid solvent, or lower.

(2) Step of Preparing a Precursor PMDA

PMDA in the prepared raw material solution is recrystallized, and the acetic acid solvent is separated thereby to prepare a precursor PMDA.

(2-1) Recrystallization of PMDA

By cooling of the raw material solution, a highly pure PMDA from which the impurities such as metal components and moisture are removed is recrystallized to prepare a precursor PMDA. During this operation, powder and granular precursor PMDA with further smaller amount of impurities can be prepared by cooling the raw material solution for recrystallization while stirring the raw material solution. This operation is preferably carried out in an inert gas atmosphere in order to prevent mingling of impurities such as moisture.

(2-2) Separation of an Acetic Acid Solvent

The heated raw material solution is cooled to an ordinary temperature to liberate the crystallized (solidified) PMDA and the liquid acetic acid solution, so as to separate the acetic acid solution. This operation is preferably carried out by natural cooling or cooling at a cooling speed close to this, because quick cooling promotes mingling of the acetic acid component into the crystal.

(3) Step of Performing a Degassing Treatment

The precursor PMDA is stirred in a fluidized state while heating under reduced-pressure conditions to perform a degassing treatment. By performing the degassing treatment under such conditions, acetic anhydride and the like remaining in the precursor PMDA can be efficiently removed. As described above, this operation is preferably carried out in an inert gas atmosphere.

(3-1) Setting of Heating Conditions

As heating conditions for the degassing treatment, the temperature of the precursor PMDA is predetermined to be about 120 degrees C., which is a boiling point of acetic acid, or higher and about 290 degrees C., which is a melting point of pyromellitic dianhydride, or lower. Further, because a mixed solvent of acetic anhydride and glacial acetic acid (acetic anhydride and the like) is used, the boiling point fluctuates depending on the composition thereof. In the case of a mixed solvent containing acetic anhydride and glacial acetic acid at an approximately equal molar ratio, the temperature is preferably about 140 degrees C., which is a boiling point thereof, or higher. The upper limit temperature for heating is preferably a low temperature because of a technical significance of reducing the loss of PMDA during the degassing treatment and reducing the loss of PMDA due to adhesion to the inner wall of the degassing treatment apparatus accompanying the rise in the vapor pressure of PMDA by high-temperature heating, recrystallization at a local low-temperature part of the apparatus, or the like. Specifically, the upper limit temperature is preferably 160 to 170 degrees C.

(3-2) Setting of Reduced-Pressure Conditions

As reduced-pressure conditions for the degassing treatment, the pressure is preferably sufficient for performing the degassing treatment of removing acetic anhydride and the like, and it is preferable to achieve reduction of the amount of evaporation without generating the melting of PMDA. Because it is preferable that the reduced-pressure conditions can be constructed by a simple means, pressure conditions of 100 Torr or lower, specifically, are preferable.

(3-3) Setting of Fluidizing and Stirring Conditions

Further, the present inventors have found out that stirring in a fluidized state is effective in the degassing treatment in the present production method. As will be described later, it is extremely difficult to perform a treatment of removing acetic anhydride and the like remaining in the recrystallized precursor PMDA, and the degassing treatment performed for a long period of time increases the loss of PMDA. The present inventors have obtained a finding that the effect of evaporation of acetic anhydride and the like from the surface of PMDA by stirring in a fluidized state is extremely effective in the degassing treatment of a short period of time, also from the later-described verification results.

A construction example of an apparatus 10 that performs the above degassing treatment is shown in FIG. 2. A stirring container 11 into which the precursor PMDA (Sp) is charged is rotated by a driving unit 12 to perform stirring in a fluidized state. Around the stirring container 11, a heating unit 13 having a heating means (not illustrated) and a heat insulator (not illustrated) is disposed, whereby a heated state at a predetermined temperature can be maintained. The stirring container 11 is provided with a gas outlet 14 and an on-off valve 15 that can be connected to an evacuation unit (not illustrated), whereby a desired pressure-reducing treatment can be carried out. It has been confirmed that, by such a construction, the degassing treatment can be carried out with certainty by stirring the precursor PMDA (Sp) in a fluidized state while heating under reduced-pressure conditions, whereby a highly pure PMDA in which the concentration of residual acetic acid is low can be prepared.

(4) Step of Preparing a Highly Pure PMDA

The highly pure PMDA subjected to the degassing treatment is taken out. By performing cooling and pressure-raising of PMDA fluidized and stirred under heated and reduced-pressure conditions, a powder and granular PMDA that is present under ordinary-temperature and ordinary-pressure conditions is prepared. This operation is preferably carried out in an inert gas atmosphere in order to prevent mingling of impurities such as moisture.

(Modification of Process for Preparing Highly Pure PMDA)

FIG. 1B is a view showing another embodiment of the procedure of preparing highly pure PMDA. The procedure of preparing highly pure PMDA according to the present invention may comprise a step of bringing recrystallized pyromellitic dianhydride into contact with a substituted or unsubstituted aromatic hydrocarbon compound. This step may hereafter be referred to as "aromatic hydrocarbon compound treatment step".

When employing the aromatic hydrocarbon compound treatment step when preparing highly pure PMDA, the aromatic hydrocarbon compound treatment step is performed after "(2-1) Recrystallization of PMDA". The aromatic hydrocarbon compound treatment step is performed before "(3) Step of performing a degassing treatment".

The method for producing highly pure pyromellitic dianhydride according to the present invention comprises the step of dissolving PMDA in the acetic acid solvent, and the step recrystallizing PMDA. Impurities such as acetic acid and water are rarely mixed in the crystallized PMDA obtained by recrystallization. However, impurities may be incorporated in the crystallized PMDA during recrystallization depending on the recrystallization conditions. In such a case, a small amount of impurities may remain even if "(3) Step of performing a degassing treatment" is performed. It was found by the studies conducted by the present inventors that impurities such as acetic acid can be more effectively removed by bringing the crystallized PMDA into contact with a substituted or unsubstituted aromatic hydrocarbon compound to produce PMDA with higher purity (see the experimental results described later). It is considered that the above effect is obtained since the crystallized PMDA swell as a result of bringing the crystallized PMDA into contact with a substituted or unsubstituted aromatic hydrocarbon compound, for example.

It is considered based on the above mechanism that a sufficient effect is obtained by bringing the crystallized PMDA into contact with a substituted or unsubstituted aromatic hydrocarbon compound. Therefore, the aromatic hydrocarbon compound treatment step may be performed at an arbitrary timing as long as the aromatic hydrocarbon compound treatment step is performed after "(2-1) Recrystallization of PMDA", and performed before "(3) Step of performing a degassing treatment". It is preferable to perform the aromatic hydrocarbon compound treatment step after "(2-2) Separation of an acetic acid solvent" in order to more reliably and effectively swell the crystallized PMDA. This makes it possible to increase the concentration of the substituted or unsubstituted aromatic hydrocarbon compound around the crystallized PMDA (i.e., increase the degree of swelling of the crystallized PMDA) when bringing the crystallized PMDA into contact with the substituted or unsubstituted aromatic hydrocarbon compound. As a result, impurities incorporated in the crystallized PMDA can be more effectively removed.

The aromatic hydrocarbon compound treatment step may be implemented by recrystallizing highly pure PMDA (from which impurities such as metal components and moisture have been removed) by cooling of the raw material solution, and adding the substituted or unsubstituted aromatic hydrocarbon compound to the container. The aromatic hydrocarbon compound treatment step may be implemented by cooling the heated raw material solution to ordinary temperature to liberate crystallized (solidified) PMDA and the liquid acetic acid solution to separate the acetic acid solution, and bringing the crystallized PMDA into contact with the substituted or unsubstituted aromatic hydrocarbon compound.

The substituted or unsubstituted aromatic hydrocarbon compound used in the aromatic hydrocarbon compound treatment step is a hydrocarbon that includes one or more rings that exhibit aromaticity. The one or more rings may be either unsubstituted or substituted with an alkyl group, an alkenyl group, or the like. The substituted or unsubstituted aromatic hydrocarbon compound includes an aromatic ring in which electrons are delocalized (conjugated). Examples of the aromatic ring included in the substituted or unsubstituted aromatic hydrocarbon compound used in the aromatic hydrocarbon compound treatment step include monocyclic aromatic rings such as a benzene ring, and fused (polycyclic) aromatic rings such as a naphthalene ring, an anthracene ring, an indene ring, a biphenylene ring, a fluorene ring, a phenanthrene ring, and a pyrene ring. The entire aromatic ring may not form a conjugated system, and the aromatic ring may form a polycyclic aggregate. A plurality of aromatic rings may be bonded through one or more methylene linkages or the like. When the aromatic ring is substituted with a substituent, the number of substituents may be one or more. Examples of the substituent include a methyl group, an ethyl group, a propyl group, a vinyl group, and the like.

Specific examples of the substituted or unsubstituted aromatic hydrocarbon compound used in the aromatic hydrocarbon compound treatment step include unsubstituted benzene and benzene substituted with an alkyl group, such as benzene, toluene, ethylbenzene, styrene, cumene, o-xylene, m-xylene, p-xylene, 2-ethyltoluene, 3-ethyltoluene, 4-ethyltoluene, 1,2,3-trimethylbenzene, 1,2,4-trimethylbenzene, and 1,3,5-trimethylbenzene, unsubstituted naphthalene, naphthalene substituted with an alkyl group, unsubstituted cyclopentadiene, cyclopentadiene substituted with an alkyl group, unsubstituted indene, indene substituted with an alkyl group, and the like. It is preferable that the substituted or unsubstituted aromatic hydrocarbon compound used in the aromatic hydrocarbon compound treatment step have a boiling point of 60 to 290 degrees C., more preferably 90 to 200 degrees C., and still more preferably 110 to 170 degrees C., from the viewpoint of removability during "(3) Step of performing a degassing treatment" together with acetic acid and the like, and a reduction in PMDA loss during degassing. Examples of the substituted or unsubstituted aromatic hydrocarbon compound that is more preferable from the above point of view include benzene, toluene, xylene, and the like. Among these, toluene is particularly preferable.

(Prepared a Highly Pure PMDA)

With regard to PMDA prepared by the above production method, the concentration of acetic acid contained is 400 mass ppm or less and further can be 200 mass ppm or less, and the concentrations of metal impurities are 50 mass ppb or less. PMDA prepared by performing the aromatic hydrocarbon compound treatment step has a concentration of residual acetic acid of 100 mass ppm or less, or 50 mass ppm or less, and moreover the concentrations of metal impurities are 50 mass ppb or less. As described above, acetic anhydride and the like used for removing metal components and moisture contained in PMDA during the production process remain in PMDA though in a slight amount, thereby raising problems such as decrease in the amount of evaporation of PMDA. As shown in the later-described verification results, the present inventors have obtained a finding that, according as the concentration of acetic acid contained is higher, the decrease in the evaporation amount and the like become larger and, practically, the concentration of acetic acid contained is preferably 400 mass ppm or less. In addition, the present inventors have obtained a finding that the concentration of acetic acid contained in PMDA prepared by the above production method can further be 200 mass ppm or less, or 100 mass ppm or less, or 50 mass ppm or less.

<Verification of Method for Producing PMDA and PMDA Prepared by the Method>

In a process of verifying the method for producing PMDA and the method for using PMDA prepared by the method, the present inventors have obtained findings such as the following (i) to (vi). The present production method and PMDA prepared by the method have been found out based on such findings, and an optimum method for PMDA prepared by the method could be constructed. In addition, excellent characteristics of PMDA prepared by such a production method could be verified.

(i) Blackening of PMDA and Decrease in Amount of Evaporation Under High-Temperature Conditions With regard PMDA to conventionally used, when sublimation and evaporation were carried out for a predetermined period of time under high-temperature (about 250 degrees C. or higher) conditions, not a small amount of PMDA underwent sharp decrease in the amount of evaporation and blackening was seen though there was still a remaining amount of PMDA. FIG. 3A shows this blackened (denatured) PMDA. In addition, as a result of thermal analysis on blackened PMDA and non-blackened PMDA, the present inventors have obtained a finding that blackened PMDA is considerably inferior in the sublimation performance as compared with non-blackened PMDA, as shown in FIG. 3B.

(ii) Search for Cause of Blackening and Studies on Countermeasure

As a result of studies on the cause of this blackening, the present inventors have obtained a finding that the cause of blackening is the remaining of acetic anhydride and the like used for purifying PMDA by removing metal components and moisture. FIG. 4A shows a result of observation of the state after PMDA in which the concentration of acetic anhydride and the like contained was 10 mass ppm or less was heated at about 260 degrees C. for 24 hours. FIG. 4B shows a result of observation of the state after PMDA in which the concentration of acetic anhydride and the like contained was 4500 mass ppm was heated at about 260 degrees C. for 24 hours. It has been confirmed that, with respect to PMDA containing a large amount of acetic anhydride and the like, blackening occurred violently. In other words, the present inventors have obtained a finding that the cause of blackening is the acetic anhydride and the like remaining in PMDA, and such blackening can be prevented by reducing the amount of the acetic anhydride and the like to a predetermined amount or less.

(iii) Correlation Between Amount of Residual Acetic Anhydride and the Like and Amount of Denaturing (Blackening) of PMDA Next, verification was carried out on how much the residual amount of such acetic anhydride and the like must be reduced. In other words, the allowable amount of acetic anhydride and the like was determined from the correlation between the residual amount of acetic anhydride and the like in PMDA after purification from which metal components and moisture were removed and the amount of denaturing (blackening) of PMDA. FIG. 5 shows a relationship between the concentration of residual acetic anhydride and the like in PMDA filled in a container in PMDA supplying apparatus having multiple stages of trays and the residual ratio of PMDA (=weight after use/initial weight) after PMDA was sublimated in PMDA supplying apparatus and supplied for a predetermined period of time. The concentration of residual acetic anhydride and the like was measured by ion chromatography (IC). A linear correlation was seen between the concentration of residual acetic anhydride and the like in PMDA that was filled in the container and the residual ratio of PMDA after use. It has been found out that, according as the concentration of residual acetic anhydride and the like in PMDA filled in the container is higher, the residual ratio of PMDA after use is higher. In addition, from the results shown in FIG. 5, the present inventors have obtained a finding that the concentration of residual acetic anhydride and the like in PMDA that is filled in the container is preferably 0 to 400 mass ppm, more preferably 0 to 200 mass ppm.

(iv) Studies on Method of Separating and Removing an Acetic Anhydride and the Like In order to reduce the concentration of residual acetic anhydride and the like in PMDA, reduction of the mingling amount of acetic anhydride and the like in preparing the precursor PMDA and a treatment of reducing the amount of acetic anhydride and the like on the precursor PMDA prepared will be necessary.

First, studies on a method of separating and removing acetic anhydride and the like at the stage of preparing the precursor PMDA were carried out. It is difficult to reduce the mingling of acetic anhydride and the like into PMDA at the stage of removing impurities such as metal components and moisture by dissolving PMDA raw material in the acetic acid solvent (preparation of the raw material solution), because this leads to decrease in the function of reducing the impurities. The present inventors have made studies on a method of separating an acetic anhydride and the like by purifying PMDA dissolved in the raw material solution by the recrystallization method.

In the case of performing a purification treatment by the recrystallization method, it is known that the solvent is incorporated into the crystal in growing the crystal while evaporating the solvent. In the present production method, reduction of the amount of acetic anhydride and the like incorporated into the crystal is achieved by recrystallizing PMDA while separating the acetic acid solvent by concentrating PMDA in the raw material solution. Specifically, by preparing the raw material solution in a state close to saturation of PMDA under heating conditions of about 140 degrees C., which is a boiling point of the acetic acid solvent, or lower, and by cooling the raw material solution to an ordinary temperature, separating the acetic acid solvent in an easily releasable state and recrystallizing PMDA, so as to reduce the amount of acetic anhydride and the like incorporated into the crystal. In addition, it has been found out that, by separating the acetic acid solvent in the same manner and recrystallizing PMDA while stirring the raw material solution, mingling of acetic anhydride and the like can be reduced.

(v) Studies on Treatment of Reducing an Acetic Anhydride and the Like on the Precursor PMDA By simple evacuating or the like, it is difficult to remove the solvent incorporated into the crystal prepared by recrystallization. For this reason, it takes a long period of time to remove the acetic anhydride and the like to a low concentration from PMDA purified by recrystallization using the acetic anhydride and the like as a solvent. The present inventors have made studies on the treatment of reducing an acetic anhydride and the like on the precursor PMDA purified by recrystallization using an acetic acid solvent and, as a result, have found out that the acetic anhydride and the like in the crystal can be removed in a short period of time by evacuating under heating conditions while stirring the crystal of PMDA in a fluidized state. Specifically, in the above step (3) of performing a degassing treatment, three conditions of (3-1) heating conditions, (3-2) reduced-pressure conditions, and (3-3) fluidizing and stirring conditions were verified. Table 1 exemplifies conditions verified on the case (fluidizing and stirring method) in which stirring is carried out in a fluidized state and the case (static method) of a static state.

TABLE 1

Acetic acid removing treatment conditions

| Treatment | Temperature (° C.) | Pressure (torr) | Flow rate of Carrier gas (sccm) | Stirring rate (rpm) |
|---|---|---|---|---|
| Fluidizing and stirring method | 120 | 10 | 0 | 50 |
| Static method | 120 | 10 | 200 | 0 |

FIG. 6 and Table 2 shows the concentration of acetic anhydride and the like in PMDA when the precursor PMDA was subjected to an evacuating treatment under heating conditions using the fluidizing and stirring method and the static method. As shown by this result, it has been confirmed that the evacuating treatment carried out under heating conditions by using the fluidizing and stirring method can remove the acetic anhydride and the like in an extremely effective manner. As shown above, it has been confirmed that, by using the present production method, highly pure PMDA that can be evaporated at a stable concentration for a long period of time can be prepared.

TABLE 2

Relationship between acetic acid removing treatment methods and concentration of acetic anhydride and the like

| Treatment | Treatment time (hr) | Concentration of Acetic anhydride (wt. ppm) | |
|---|---|---|---|
| | | Before treatment | After treatment |
| Fluidizing and stirring method 1 | 60 | 5600 | 300 |
| Fluidizing and stirring method 2 | 60 | 5600 | 330 |
| Static method 1 | 72 | 6400 | 4000 |
| Static method 2 | 72 | 6400 | 4500 |

(vi) Study of Treatment of Reducing Acetic Acid and the Like on Precursor PMDA

It was found that the concentration of acetic anhydride and the like could be reduced to about 300 to 330 mass ppm using the fluidizing and stirring method (see (v)). The present inventors also conducted studies regarding a method that reduces acetic acid and the like in precursor PMDA by bringing a substituted or unsubstituted aromatic hydrocarbon compound into contact with crystallized PMDA. It was found that impurities such as acetic acid and acetic anhydride in crystallized PMDA can be further reduced within a short time by bringing a substituted or unsubstituted aromatic hydrocarbon compound into contact with crystallized PMDA, and stirring the mixture.

Specifically, precursor PMDA was immersed in excess toluene for 3 hours before performing the step (3) of performing the degassing treatment. The mixture (slurry) was filtered to obtain precursor PMDA treated with toluene. The precursor PMDA treated with toluene and the precursor PMDA that was not treated with toluene were stirred in a fluidized state while heating at 160 degrees C. under reduced-pressure conditions (see above). The precursor PMDA treated with toluene was stirred for 48 hours, and the precursor PMDA that was not treated with toluene was stirred for 60 hours. The concentration of acetic acid in each PMDA was measured by GC (gas chromatography)-FID (flame ionization detector) method. The results are shown in Table 3. Note that the precursor PMDA was purchased from Daicel Ltd. The precursor PMDA was dissolved in an acetic acid solvent, and recrystallized. The total amount of acetic acid, acetic anhydride, and the like (i.e., components derived from the acetic acid solvent) in PMDA was evaluated by measuring the concentration of acetic acid.

TABLE 3

Relationship between acetic acid removing treatment methods and concentration of acetic acid

| Treatment method | Acetic acid concentration (wt. ppm) |
|---|---|
| Before treatment | 756 |
| Fluidizing and stirring method | 232 |
| Treatment with toluene + fluidizing and stirring method | 46 |

As shown in Table 3, it was confirmed that acetic acid and the like were more effectively removed when the precursor PMDA was brought into contact with toluene (substituted aromatic hydrocarbon compound), and stirred in a fluidized state, as compared with the case where the precursor PMDA was merely stirred in a fluidized state. Specifically, the concentration of the residual acetic acid and the like could be significantly reduced (about ⅕th) when the precursor PMDA was brought into contact with toluene (aromatic hydrocarbon compound), and stirred in a fluidized state, as compared with the case where the precursor PMDA was merely stirred in a fluidized state. It was also found that the concentration of acetic acid and the like could be sufficiently reduced even when the fluidizing and stirring time was reduced. It was thus confirmed that highly pure PMDA that can be evaporated at a stable concentration for a long period of time can be prepared by utilizing the above production method.

(vii) Study of Treatment of Reducing Metal Impurities on Precursor PMDA

The concentration of metal impurities in crude and treated PMDA were measured by ICP-MS (Inductively Coupled Plasma Mass Spectrometry) method. It was found that the concentration of metal impurities are reduced to about 50 mass ppb using the fluidizing and stirring method (see (v)) and the fluidizing and stirring method with toluene treatment (see (vi)). Specifically, B, Co, Cr, Mn, Ti, Zn are reduced to about 50 mass ppb as shown in Table 4.

TABLE 4

The concentration of metal impurities in crude and treated PMDA were measured by ICP-MS method

| | Crude PMDA | | | | | | | | | |
|---|---|---|---|---|---|---|---|---|---|---|
| | Lot No. 1 | | Lot No. 1 Treatment | | Lot No. 2 | | Lot No. 2 | | Lot No. 2 | |
| | Before treatment | | Fluidizing and stirring method | | Before treatment | | Fluidizing and stirring method | | Treatment with toluene + Fluidizing and stirring method | |
| | wt · ppb | | wt · ppb | | wt · ppb | | wt · ppb | | wt · ppb | |
| Element | DL | Conc. | DL | Conc. | DL | Conc. | DL | Conc. | DL | Conc. |
| B  | 30 | 79    | 19 | 50    | 30 | 84    | 200 | <DL | 200 | <DL |
| Cd | 30 | <DL   | 5  | <DL   | 30 | <DL   | 2   | <DL | 2   | <DL |
| Co | 30 | <DL   | 8  | <DL   | 30 | 397   | 1   | 44  | 1   | 33  |
| Cr | 30 | 78    | 6  | 21    | 30 | <DL   | 10  | <DL | 20  | <DL |
| K  | 30 | <DL   | 6  | <DL   | 30 | <DL   | 10  | <DL | 20  | <DL |
| Li | 30 | <DL   | 20 | <DL   | 30 | <DL   | 10  | <DL | 10  | <DL |
| Mn | 30 | 194   | 6  | 12    | 30 | 283   | 1   | 43  | 1   | 24  |
| Ni | 30 | <DL   | 30 | <DL   | 30 | <DL   | 10  | <DL | 10  | <DL |
| Pb | 30 | <DL   | 8  | <DL   | 30 | <DL   | 10  | <DL | 10  | <DL |
| Ti | 30 | <DL   | 20 | <DL   | 30 | 46    | 5   | <DL | 5   | <DL |
| V  | 30 | <DL   | 7  | <DL   | 30 | <DL   | 2   | <DL | 2   | <DL |
| Zn | 30 | 56    | 11 | 15    | 30 | 62    | 2   | 9   | 2   | 31  |

(DL = detection limit)

<Apparatus and Method for Supplying PMDA According to the Present Invention>

Embodiments of an apparatus for supplying PMDA according to the present invention (hereafter referred to as "present supplying apparatus") and a method for supplying PMDA using this apparatus (hereafter referred to as "present supplying method") will be described with reference to the drawings. The present supplying apparatus is characterized in that PMDA prepared by the present production method described above is used; the apparatus comprises a sample placing unit for placing a sample tray into which PMDA is charged is placed, a supplying unit for supplying a carrier gas, a dispersing unit for dispersing the supplied carrier gas, and an outputting unit for outputting gaseous PMDA prepared in the sample placing unit; and the powder and granular PMDA placed in the sample placing unit is evaporated under predetermined temperature conditions, dispersed under atmospheric pressure or reduced-pressure conditions of a carrier gas atmosphere to be entrained by the carrier gas, and outputted as gaseous PMDA. Note that PMDA used for the present supplying apparatus may or may not have been treated with toluene.

As the carrier gas, a gas having a low reactivity and a high stability is preferable and, for example, a rare gas such as helium or argon, nitrogen gas, or the like can be used. Further, in order to perform sublimation of PMDA in a stable manner, a carrier gas having a large heat capacity is preferable, and argon gas is suitable.

(Construction Example of Apparatus for Supplying PMDA)

A construction example of the present supplying apparatus is shown in FIG. 7. The present supplying apparatus comprises a supplying unit 1 for supplying a carrier gas C, a dispersing unit 2 for dispersing the supplied carrier gas C, a sample placing unit 3 in which a tray 3a for placing a sample into which a powder and granular PMDA(S) is charged is placed, and an outputting unit 4 for outputting a gaseous PMDA (hereafter referred to as "PMDA gas") G. In addition, a heating unit 5 for heating the present supplying apparatus from outside is preferably provided. By heating PMDA(S) to a predetermined temperature, sublimation (evaporation) of PMDA(S) is promoted, whereby PMDA gas G having a predetermined material concentration can be supplied. Thus, a highly pure PMDA can be supplied at a stable concentration for a long period of time.

The PMDA(S) to be treated is charged in a predetermined amount into the tray 3a from a material supplying unit (not illustrated) of the present supplying apparatus. The shape or the like of PMDA(S) is not particularly limited; however, it is preferably a shape that is molded to have a granular shape, a pellet shape, a porous shape, a honeycomb shape, or the like having a large area of contact with the carrier gas C and having a smaller flow passage resistance. With respect to PMDA(S) charged into the tray 3a, the amount of decrease by sublimation is grasped, and replenishment or replacement is carried out at a predetermined time interval.

(Method for Supplying PMDA Gas Using the Present Supplying Apparatus)

The present supplying method is characterized in that PMDA prepared by the present production method described above is supplied by using the present supplying apparatus described above, according to the following steps:

(1) a step of providing a powder and granular PMDA, (2) a step of placing in the sample placing unit a sample tray into which the powder and granular PMDA is charged, (3) a step of supplying a carrier gas to the supplying unit, (4) a step of heating the sample placing unit in the carrier gas atmosphere to temperature conditions corresponding to a desired vapor pressure of PMDA, and (5) a step of outputting a gaseous PMDA entrained by the supplied carrier gas under desired predetermined pressure conditions.

By charging a predetermined amount of PMDA(S) into the tray 3a, introducing the carrier gas C in a state in which the tray 3a is heated to a predetermined temperature, and taking out PMDA gas G having a predetermined material concentration, highly pure PMDA that can be evaporated at a stable concentration for a long period of time can be prepared.

The carrier gas C is supplied from the supplying unit 1 into the present supplying apparatus. The pressure and the flow rate of the supplied carrier gas C are adjusted to predetermined values that are set in advance by specification. Adjustment of the pressure and flow rate conditions is limited neither to the time before supplying to the present supplying apparatus nor to the time after outputting from the present supplying apparatus. The carrier gas C supplied into the present supplying apparatus is first introduced to the sample placing unit 3 in a state of being dispersed by the dispersing unit 2 connected to the supplying unit 1. At this time, the carrier gas C is branched at a horizontal cross-section of the sample placing unit 3 in a state of being heated and maintained to a predetermined temperature by the dispersing unit 2, so that the carrier gas C can be widely dispersed into the sample placing unit 3. The carrier gas C introduced into the sample placing unit 3 heats PMDA(S) that is charged into the tray 3a to a predetermined temperature, so as to generate PMDA gas having a predetermined vapor pressure. At this time, a state of having an approximately uniform temperature and flow rate can be formed at any site of the sample placing unit 3 by the carrier gas C dispersed in the sample placing unit 3.

The carrier gas C heated and maintained to a predetermined temperature is introduced to the tray 3a and, by contact with PMDA(S) in the tray 3a, PMDA gas G sublimating and having a desired vapor pressure of PMDA is prepared. By setting the flow rate of the carrier gas C and the volume of the tray 3a to attain a desired spatial speed in advance, sufficient contact time can be ensured, and PMDA gas G having a stable material concentration can be obtained. PMDA gas G prepared at a desired material concentration by being mixed and uniformized is entrained by the carrier gas C and outputted from the outputting unit 4.

<Verification of Functions in the Present Supplying Apparatus and the Present Supplying Method>

The functions in the present supplying apparatus and the present supplying method were verified as follows by using a supplying apparatus 20 exemplified in FIG. 8. Change in the evaporation amount was compared between PMDA prepared by the present production method and PMDA prepared by the conventional static method described above, so as to re-verify the demonstration results in the present production method. The supplying apparatus 20 comprises a container 21 into which PMDA(S) is placed, on-off valves V1, V2, Vs, and a flow rate controlling unit 22 that undertake supply of the carrier gas C to the container 21, a decompression pump 23 that degasses the inside of the container 21 via an on-off valve V3 to provide a reduced-pressure state, a pressure sensor 24 that senses the pressure in the inside of the container 21, and a thermal conduction sensor 25 that measures the concentration of PMDA in PMDA gas G, whereby PMDA gas G is supplied to consumption equipment 30.

(i) Verification Conditions

In the same manner as in the present supplying apparatus, the container 21 having multiple stages of trays was filled with PMDA(So) prepared by the present production method (fluidizing and stirring method) (that was not treated with toluene) and PMDA(Sr) prepared by the static method. The concentration of PMDA in the outputted gas when heated and sublimated was monitored by using the thermal conduction sensor 25 (type GC-8A manufactured by Shimadzu Corporation). PMDA(So) and PMDA(Sr) were subjected to a degassing treatment under conditions shown in the following Table 5.

Specifically, verification was carried out by the following procedure.

(i-1) The container 21 is filled with 217 g of PMDA(So) and 217 g of PMDA(Sr).

(i-2) The on-off valves V1, V2, Vs are opened, and a carrier gas C adjusted to have a predetermined flow rate by the flow rate controlling unit 22 is introduced into the container 21. The introduced carrier gas C entrains PMDA gas sublimated in the supplying apparatus 20 and is guided to the thermal conduction sensor 25. By measuring the concentration of PMDA gas with use of the thermal conduction sensor 25, the amount of evaporation of PMDA per unit period of time is measured.

(i-3) The container 21 was heated to 260 degrees C. and, in a state in which sublimation was carried out continuously for 56 hours, the concentration of PMDA was monitored by the thermal conduction sensor 25.

TABLE 5

| Acetic acid removing treatment conditions | | | | | |
|---|---|---|---|---|---|
| Treatment | Temperature (° C.) | Pressure (torr) | Flow rate of Carrier gas (sccm) | Stirring rate (rpm) | Treatment time (hr) |
| Fluidizing and stirring method | 120 | 10 | 0 | 50 | 60 |
| Static method | 120 | 10 | 200 | 0 | 72 |

(ii) Verification Results

The concentrations of acetic anhydride and the like remaining in PMDA(So) and PMDA(Sr) subjected to the degassing treatment were 360 mass ppm and 4500 mass ppm, respectively. As a result of the above verification, FIG. 9 shows a correlation between a filling ratio (ratio of residual amount) and an amount of evaporation of PMDA. With respect to PMDA(So), the amount of evaporation of PMDA was stable up to the filling ratio of 95%, thereby confirming that a supply of PMDA at a constant concentration can be made. On the other hand, with respect to PMDA(Sr) from which acetic anhydride and the like were removed by the static method, it has been confirmed that the amount of evaporation decreased at least at the filling ratio of 20%. As shown above, it has been confirmed that a supply of PMDA at a constant concentration can be made by the present supplying apparatus, and that the amount of evaporation of PMDA prepared by the present production method has an extremely high stability, so that a supply of PMDA at a stable concentration for a long period of time can be made.

REFERENCE SIGNS LIST

1: Supplying unit, 2: Dispersing unit, 3: Sample placing unit, 4: Outputting unit, 5: Heating unit, C: Carrier gas, G: PMDA gas, S: PMDA(S)

The invention claimed is:

1. A method for producing pyromellitic dianhydride having an acetic acid content of 400 mass ppm or less, the method comprising:
(1) preparing a raw material solution by dissolving a pyromellitic dianhydride raw material in an acetic acid solvent,
(2) recrystallizing pyromellitic dianhydride from the raw material solution and separating the acetic acid solvent to produce recrystallized pyromellitic dianhyrdride,
(2a) stirring the recrystallized pyromellitic dianhydride in a substituted or unsubstituted aromatic hydrocarbon compound and filtering to separate a swollen recrystallized pyromellitic dianhydride from the substituted or unsubstituted aromatic hydrocarbon;
(3) degassing the swollen recrystallized pyromellitic dianhydride by stirring the swollen recrystallized pyromellitic dianhydride in a fluidized state while heating to a temperature between about 120° C. to about 290° C. under reduced pressure of 100 Torr or less to produce degassed pyromellitic dianhydride, and
(4) cooling the degassed pyromellitic dianhydride to ordinary temperature conditions under an inert gas atmosphere while returning to ordinary pressure conditions to produce the pyromellitic dianhydride having an acetic acid content of 400 mass ppm or less.

2. The method of claim 1, wherein the raw material solution is prepared under heated conditions of about 140° C.

3. The method of claim 1, wherein the raw material solution is cooled to an ordinary temperature to recrystallize the pyromellitic acid.

4. The method of claim 3, wherein the raw material solution is cooled by natural cooling or cooling at a cooling speed close to natural cooling.

5. The method of claim 1, wherein the pyromellitic dianhydride has an acetic acid content of 200 mass ppm or less.

6. The method of claim 1, wherein the pyromellitic dianhydride has an acetic acid content of 100 mass ppm or less.

7. The method of claim 1, wherein the pyromellitic dianhydride has an acetic acid content of 50 mass ppm or less.

8. The method of claim 1, wherein the acetic acid solvent is a mixed solution of acetic anhydride and glacial acetic acid.

9. The method of claim 1, wherein the method is performed under an inert gas atmosphere.

10. The method of claim 1, further comprising stirring the raw material solution during the step (2) recrystallizing step.

11. The method of claim 1, wherein the substituted or unsubstituted aromatic hydrocarbon compound is toluene or benzene.

12. The method of claim 11, wherein the substituted or unsubstituted aromatic hydrocarbon compound is toluene.

* * * * *